(12) United States Patent
Aiba et al.

(10) Patent No.: US 7,393,395 B2
(45) Date of Patent: Jul. 1, 2008

(54) SURFACE-TREATING AGENT FOR METAL

(75) Inventors: Akihiro Aiba, Kitaibaraki (JP); Tomoharu Mimura, Kitaibaraki (JP)

(73) Assignee: Nippon Mining & Metals Co., Ltd., Tokyo (JP)

( * ) Notice: Subject to any disclaimer, the term of this patent is extended or adjusted under 35 U.S.C. 154(b) by 11 days.

(21) Appl. No.: 10/587,003

(22) PCT Filed: Jan. 21, 2005

(86) PCT No.: PCT/JP2005/000755

§ 371 (c)(1), (2), (4) Date: Jul. 20, 2006

(87) PCT Pub. No.: WO2005/075706

PCT Pub. Date: Aug. 18, 2005

(65) Prior Publication Data
US 2007/0157845 A1    Jul. 12, 2007

(30) Foreign Application Priority Data
Feb. 5, 2004    (JP) ............................ 2004-028905

(51) Int. Cl.
*C23F 11/14*    (2006.01)
(52) U.S. Cl. ............. 106/14.16; 106/14.15; 106/14.17; 106/14.44; 252/389.5; 252/389.52; 252/389.53; 252/389.54; 252/394
(58) Field of Classification Search ............ 106/14.15, 106/14.44, 14.16, 14.17; 252/394, 389.5, 252/389.52, 389.53, 389.54
See application file for complete search history.

(56) References Cited

U.S. PATENT DOCUMENTS

| | | | | |
|---|---|---|---|---|
| 3,408,307 | A | * | 10/1968 | Troscinski et al. ........... 252/394 |
| 4,142,029 | A | * | 2/1979 | Illy ............................. 521/95 |
| 5,744,069 | A | * | 4/1998 | Maeda et al. ................ 252/394 |
| 6,156,906 | A | * | 12/2000 | Hyoda et al. ................. 548/250 |
| 6,433,181 | B1 | * | 8/2002 | Hyoda et al. ................. 548/250 |
| 6,517,647 | B1 | * | 2/2003 | Yamato ........................ 149/45 |
| 2004/0016363 | A1 | | 1/2004 | Phelps et al. |

FOREIGN PATENT DOCUMENTS

| | | | |
|---|---|---|---|
| EP | 1035118 | A1 * | 9/2000 |
| EP | 1241138 | A1 * | 9/2002 |
| JP | 4-160173 | | 6/1992 |
| JP | 4-206681 | | 7/1992 |
| JP | 7-33754 | A * | 2/1995 |
| JP | 7-145491 | | 6/1995 |
| JP | 7-243053 | | 9/1995 |
| JP | 2575242 | | 10/1996 |
| JP | 8-311658 | | 11/1996 |
| JP | 2686168 | | 8/1997 |
| JP | 10-246962 | A * | 9/1998 |
| JP | 11-508927 | | 8/1999 |
| JP | 2000-282033 | | 10/2000 |
| JP | 3141145 | | 12/2000 |
| JP | 2001-348377 | | 12/2001 |
| JP | 3373356 | | 11/2002 |
| JP | 2002-543294 | | 12/2002 |
| JP | 2003-3283 | | 1/2003 |
| JP | 2003-502322 | | 5/2003 |
| JP | 2005-60754 | | 3/2005 |

* cited by examiner

*Primary Examiner*—Anthony J. Green
(74) *Attorney, Agent, or Firm*—Flynn, Thiel, Boutell & Tanis, P.C.

(57) ABSTRACT

The present invention provides a surface-treating agent which improves heat resistance, adhesiveness to resin and solder wettability. The surface-treating agent for metal contains a tetrazole derivative represented by the following formula and/or a salt thereof,

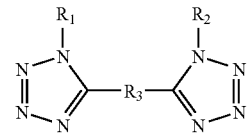

wherein $R_1$ and $R_2$ each independently represent a hydrogen atom, a halogen atom, or an alkyl group or an aryl group, etc., which each have a carbon number of not more than 10, and a group having a halogen atom, a hydroxyl group, a carboxyl group, an amino group or a mercapto group added thereto, or represent an amino group, a mercapto group, a hydroxyl group or a carboxyl group; and $R_3$ represents a bond or an alkylene group, etc., which each have a carbon number of not more than 10, and a group having a halogen atom, a hydroxyl group, a carboxyl group, an amino group, a mercapto group, an azo group (—N=N—), a sulfide group (—S—), or a disulfide group (—S—S—) added thereto, or represents an azo group, a sulfide group, or disulfide group, and may contain a metal or metal compound.

11 Claims, No Drawings

SURFACE-TREATING AGENT FOR METAL

TECHNICAL FIELD

The present invention relates to a surface-treating agent for metal.

BACKGROUND ART

Triazoles and derivatives thereof are well-known agents to prevent discoloration of copper and copper alloys. Such compounds, arranged for use in electronic materials, include an acidic solution to prevent copper discoloration proposed by the present applicants, which contains 5-methyl-1H-benzotriazole, 5,6-dimethyl-1H-benzotriazole, or 2-mercaptopyrimidine (Patent Document 1 (Japanese Patent Publication No. H04-160173)). Although the compounds have excellent moisture resistance and effectively prevent copper discoloration during storage of treated products, they are susceptible to heat, which is problematic in that copper is oxidized by heating and this results in the oxide film peeling. The present applicants solved this problem in the application of Patent Document 2 (Japanese Patent No. 3373356), which is a solution to prevent copper discoloration obtained by adding a metal more noble than copper, or a salt thereof, to a solution of a heterocyclic compound containing nitrogen and/or sulfur in the molecule and acting as an inhibitor of copper. However, this surface-treating agent, though avoiding the peeling of the oxidized film, does not prevent copper oxidation upon heating.

Substances to suppress copper oxidation during heating and to improve solder wettability include, for instance, a benzimidazole modified at the 2-position (Patent Document 3 (Japanese Patent No. 2575242), Patent Document 4 (Japanese Patent No. 2686168)), or an imidazole derivative (Patent Document 5 (Japanese Patent Publication No. H04-206681), Patent Document 6 (Japanese Patent Publication No. H07-243053)). However, these involve thick films of several tenths of microns to several microns, which have therefore low adhesiveness to resins. To solve this problem, Non-Patent Document 1 (Journal of Technical Disclosure No. 2003-502332) suggests a mercaptobenzoxazole derivative and a mercaptobenzothiazole derivative as a surface-treating agent.

Surface-treating agents containing a tetrazole compound have also been proposed. For instance, Patent Document 7 (Japanese Patent No. 3141145) proposes a tetrazole-based compound, Patent Document 8 (Japanese Patent Publication No. 2000-282033) proposes a surface treating agent comprising a tetrazole-based compound and a thiadiazole-based compound, Patent Document 9 (Japanese Patent Publication No. 2003-3283) proposes roughening a copper surface by a surface-treating agent containing hydrogen peroxide, mineral acid, tetrazole compound, silver ion, and halogen ion, in order to increase the adhesiveness to resins. The present applicants have proposed a surface-treating agent containing a tetrazole compound and a halogen compound (Patent Document 10 (Japanese Patent Application No. 2003-290346)).

Patent Document 1: Japanese Patent Publication No. H04-160173
Patent Document 2: Japanese Patent No. 3373356
Patent Document 3: Japanese Patent No. 2575242
Patent Document 4: Japanese Patent No. 2686168
Patent Document 5: Japanese Patent Publication No. H04-206681
Patent Document 6: Japanese Patent Publication No. H07-243053
Patent Document 7: Japanese Patent No. 3141145
Patent Document 8: Japanese Patent Publication No. 2000-282033
Patent Document 9: Japanese Patent Publication No. 2003-3283
Patent Document 10: Japanese Patent Application No. 2003-290346
Non-Patent Document 1: Journal of Technical Disclosure No. 2003-502332

DISCLOSURE OF THE INVENTION

An object of the present invention is to provide a surface-treating agent which further improves heat resistance, adhesiveness to a resin, and solder wettability.

As a result of diligent research, the inventors perfected the present invention upon finding that surface treatment by a specific tetrazole derivative is more effective.

Specifically, the present invention relates to (1) a surface-treating agent for metal, comprising a tetrazole derivative represented by a below general formula and/or a salt thereof.

Chemical Formula 1

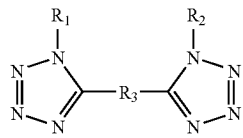

(wherein $R_1$ and $R_2$ each independently represent a hydrogen atom, a halogen atom, or an alkyl group, alkenyl group, alkinyl group, aryl group, aralkyl group or benzyl group, which each have a carbon number of not more than 10, and a group having added thereto a halogen atom, a hydroxyl group, a carboxyl group, an amino group or a mercapto group, or represent an amino group, a mercapto group, a hydroxyl group or a carboxyl group; and $R_3$ represents a bond or an alkylene group, alkenylene group, alkynylene group, arylene group or aralkylene group, which each have a carbon number of not more than 10, and a group having added thereto a halogen atom, a hydroxyl group, a carboxyl group, an amino group, a mercapto group, an azo group, a sulfide group or a disulfide group, or represents an azo group (—N═N—), a sulfide group (—S—), or a disulfide group (—S—S—); and (2) a surface-treating agent for metal according to (1), further containing a metal or a metal compound.

BEST MODE FOR CARRYING OUT THE INVENTION

The metal surface-treating agent of the present invention contains, as an active component, the tetrazole derivative and/or salts thereof represented by the above general formula, preferred examples of which include the compounds listed below and salts thereof. Though not particularly limited thereto, preferred salts include salts of alkaline metal salts, alkaline earth metal salts, ammonium salts and amine salts.

5,5'-bi-1H-tetrazole, 5,5'-bi-1-methyltetrazole, 5,5'-bi-1-phenyltetrazole, 5,5'-bi-1-mercaptotetrazole, 5,5'-bi-1-chlorotetrazole, 5,5'-ethylenebis-1H-tetrazole, 5,5'-ethylenebis-1-methyltetrazole, 5,5'-ethylenebis-1-phenyltetrazole, 5,5'-ethylenebis-1-mercaptotetrazole, 5,5'-ethylenebis-1-chlorotetrazole, 5,5'-azobis-1H-tetrazole, 5,5'-azobis-1-methyltetrazole, 5,5'-azobis-1-phenyltetrazole, 5,5'-azobis-1-mercaptotetrazole, 5,5'-azobis-1-chlorotetrazole, 5,5'-disulfidebis-1H-tetrazole, 5,5'-disulfidebis-1- methyltetrazole, 5,5'-disulfidebis-1-phenyltetrazole, 5,5'-disulfidebis-1-mercaptotetrazole, 5,5'-disulfidebis-1-chlorotetrazole, or the like.

These tetrazole derivatives can be used as a mixture of two or more thereof, and the surface-treating agent of the present invention may contain the derivative in an amount of from 0.05 to 100 g/L, preferably 0.1 to 50 g/L.

An amount below 0.05 g/L results in low film-forming ability and precludes achieving good characteristics. An amount above 100 g/L is not advantageous, as it merely increases solution losses through transfer, etc.

The surface-treating agent of the present invention can gain enhanced effects by the addition of another metal or metal compound, as well as the tetrazole derivative. Such metals or metal compounds include, preferably, zinc, manganese, chromium, tin, iron, nickel, cobalt, copper, gold, silver, platinum, palladium, rhodium, ruthenium, or compounds thereof. The metal or metal compound can be used as a mixture of two or more thereof. The surface-treating agent of the present invention contains 1 mg/L to 100 g/L, preferably 10 mg/L to 20 g/L of the metal or metal compound.

An amount below 1 mg/L results in a low enhancement effect as regards to heat resistance, adhesiveness to a resin, and solder wettability, whereas an amount above 100 g/L is not advantageous, as it merely increases solution losses through transfer, etc.

Examples of the aforementioned metal compounds include the compounds below.

Zinc compounds include, for instance, zinc hydroxide, zinc oxide, zinc formate, zinc acetate, zinc chloride, zinc sulfide and zinc phosphate; manganese compounds include, for instance, manganese hydroxide, manganese oxide, manganese chloride, manganese sulfate, manganese formate and manganese acetate; chromium compounds include, for instance, chromium hydroxide, chromium oxide, chromic acid, bichromic acid, chromium chloride, chromium sulfate, chromium phosphate, chromium acetate, chromium bromide and chromium iodide.

Tin compounds include, for instance, tin hydroxide, tin oxide, tin formate, tin acetate, tin chloride, tin bromide and tin iodide; iron compounds include, for instance, iron hydroxide, iron oxide, iron formate, iron acetate, iron chloride, iron bromide and iron iodide; nickel compounds include, for instance, nickel hydroxide, nickel oxide, nickel chloride, nickel formate, nickel acetate, nickel bromide and nickel iodide; cobalt compounds include, for instance, cobalt hydroxide, cobalt oxide, cobalt chloride, cobalt formate, cobalt acetate, cobalt bromide and cobalt iodide.

Copper compounds include, for instance, copper hydroxide, copper oxide, copper chloride, copper sulfate, copper phosphate, copper carbonate, copper formate, copper acetate, copper oxalate, copper bromide and copper iodide; gold compounds include, for instance, gold chloride, chloroauric acid, gold bromide, gold iodide, gold sulfite, gold thiosulfate, gold cyanide, potassium gold cyanide and sodium gold cyanide; silver compounds include, for instance, silver hydroxide, silver oxide, silver nitrate, silver iodide, silver bromide, silver succinimide, silver hydantoin, silver cyanide, potassium silver cyanide and sodium silver cyanide; platinum compounds include, for instance, platinum chloride and chloroplatinic acid.

Palladium compounds include, for instance, palladium hydroxide, palladium oxide, palladium chloride, chloropalladic acid, palladium iodide and palladium sulfate; rhodium compounds include, for instance, rhodium hydroxide, rhodium oxide, rhodium chloride, chlororhodic acid, rhodium iodide and rhodium sulfate; ruthenium compounds include, for instance, ruthenium hydroxide, ruthenium oxide, ruthenium chloride, chlororuthenic acid, ruthenium iodide and ruthenium sulfate.

The surface-treating agent of the present invention is provided as a solution containing as an active component thereof the above-mentioned tetrazole derivative or the tetrazole derivative plus the metal or the metal compound. The solution is preferably an aqueous solution.

The pH of the surface-treating agent of the present invention ranges from 1 to 14, preferably from 2 to 12. A pH value outside this range results in low film-forming ability and precludes exhibiting good characteristics.

The temperature when metal surface-treating with the use of the surface-treating agent of the present invention ranges from 5 to 90° C., preferably from 10 to 70° C. A temperature below 5° C. results in low film-forming ability and precludes achieving good characteristics. A temperature above 90° C. is disadvantageous as only workability becomes impaired.

As a method for surface treatment, ordinary treatment methods can be used, for instance, a method wherein the surface-treating agent is applied on the surface by dipping or brush coating, followed by solvent evaporation. The application method is not limited to the foregoing and may be any method which can provide the surface-treating agent uniformly on the surface.

The duration of the surface treatment ranges from 0.1 to 300 seconds, preferably from 10 to 120 seconds. Less than 0.1 second results in low film-forming ability and precludes achieving good characteristics. A treatment time exceeding 300 seconds does not afford any particular benefit.

Applied on a metal surface, the surface-treating agent of the present invention improves the heat resistance, adhesiveness to a resin and solder wettability of the metal surface. Metals that can be treated by the use of the surface-treating agent of the present invention include, though are not limited to, copper, silver, gold, iron, nickel and tin, or surfaces of alloys thereof, preferably copper or copper alloys.

EXAMPLES

The present invention will be explained more in detail below through Examples.

A rolled copper raw foil, measuring 100 mm×100 mm and having a thickness of 70 μm, was surface-treated by immersion in an aqueous solution of the surface-treating agent given in the tables below; thereafter, specimens prepared by cutting the foil into an appropriate size were tested as follows.

For the solder wettability test, printed wiring boards after surface treatment of dipping in a surface-treating agent solution were checked.

The results of the surface treatment were evaluated based on the following criteria:

Appearance:

○ exhibited no defective appearance, such as treatment unevenness or the like; x exhibited defective appearance.

Moisture Resistance:

Specimens were left to stand for 96 hours under an environment at 40° C. and 90% humidity, after which the presence or absence of discoloration on the copper foil surface was checked visually. ○ showed no discoloration, x showed discoloration.

Heat Resistance:

Specimens were heated for 1 hour in an oven at 170, after which the presence or absence of discoloration on the copper foil surface was inspected visually. ○ showed no discoloration, x showed discoloration.

Adhesiveness to Resin 1:

Specimens ○ had an adhesiveness (shear strength) to an epoxy molding resin equal to or higher than 10 kgf/cm², and x had an adhesiveness lower than that.

Adhesiveness to Resin 2:

Specimens ○ had an adhesiveness (90° peel strength) to an epoxy molding resin equal to or higher than 0.5 kgf/cm, and x had an adhesiveness lower than that.

Solder Wettability:

Printed wiring boards (copper line width 0.8) were allowed to stand for 96 hours in an environment at 40° C. and 90% humidity, heated for 6 hours at 175° C., and then treated with post-flux (R type); thereafter, tin-lead eutectic solder balls having a diameter of 0.6 mm were placed on the copper circuit portions, and the boards were reflowed. Specimens ○ showed a solder wetting length of 3 mm or more, Δ showed 2 mm or more, and x meant less than 2 mm.

TABLE 1

|  | Example | | | |
|---|---|---|---|---|
|  | 1 | 2 | 3 | 4 |
| Bath composition | | | | |
| Main component | 5,5'-bi-1H-tetrazole: 1.0 g/L | 5,5'-bi-1-methyl tetrazole: 1.0 g/L | 5,5'-azobis-1H-tetrazole: 1.0 g/L | 5,5'-azobis-1-methyl tetrazole: 1.0 g/L |
| Metal compound | — | — | — | — |
| Treatment condition | | | | |
| pH | 5.0 | 5.0 | 5.0 | 5.0 |
| Treatment temperature (° C.) | 25 | 25 | 25 | 25 |
| Treatment duration (s) | 30 | 30 | 30 | 30 |
| Evaluation results | | | | |
| Appearance | ○ | ○ | ○ | ○ |
| Moisture resistance | ○ | ○ | ○ | ○ |
| Heat resistance | ○ | ○ | ○ | ○ |
| Adhesiveness to resin 1 | ○ | ○ | ○ | ○ |
| Adhesiveness to resin 2 | ○ | ○ | ○ | ○ |
| Solder wettability | Δ | Δ | Δ | Δ |

TABLE 2

|  | Example | | | |
|---|---|---|---|---|
|  | 5 | 6 | 7 | 8 |
| Bath composition | | | | |
| Main component | 5,5'-bi-1H-tetrazole: 1.0 g/L | 5,5'-bi-1-methyl tetrazole: 1.0 g/L | 5,5'-azobis-1H-tetrazole: 1.0 g/L | 5,5'-azobis-1-methyl tetrazole: 1.0 g/L |
| Metal compound | Palladium chloride: 1.0 g/L (Pd) | Silver iodide: 1.0 g/L (Ag) | Gold sulfite: 1.0 g/L (Ag) | Palladium chloride: 1.0 g/L (Pd) |
| Treatment condition | | | | |
| pH | 5.0 | 5.0 | 5.0 | 5.0 |
| Treatment temperature (° C.) | 25 | 25 | 25 | 25 |
| Treatment duration (s) | 30 | 30 | 30 | 30 |
| Evaluation results | | | | |
| Appearance | ○ | ○ | ○ | ○ |
| Moisture resistance | ○ | ○ | ○ | ○ |
| Heat resistance | ○ | ○ | ○ | ○ |
| Adhesiveness to resin 1 | ○ | ○ | ○ | ○ |
| Adhesiveness to resin 2 | ○ | ○ | ○ | ○ |
| Solder wettability | ○ | ○ | ○ | ○ |

TABLE 3

|  | Comparative Example | | | |
|---|---|---|---|---|
|  | 1 | 2 | 3 | 4 |
| Bath composition | | | | |
| Main component | 2,4-diphenyl imidazole: 2 g/L | 5-amino-1H-tetrazole: 3 g/L | 1-methyl-5-aminotetrazole: 0.5 g/L | 1-methyl-5-mercaptotetrazole: 20 g/L |
| Metal salt | Copper acetate Cu: 150 mg/L | Silver nitrate Ag: 0.2 mg/L | — | 1-mercapto-5-methyl-1,3,4-thiadiazole: 20 g/L |

TABLE 3-continued

| | Comparative Example | | | |
|---|---|---|---|---|
| | 1 | 2 | 3 | 4 |
| Others | Potassium iodide: 150 mg/L Acetic acid: 50 g/L | Sodium chloride: 0.3 mg/L Hydrogen peroxide: 20 g/L Sulfuric acid: 90 g/L | — | Polyethylene glycol condensation-type nonionic surfactant: 50 g/L Triethanolamine: 40 g/L |
| Treatment condition | | | | |
| pH | 3.5 | <1 | 3.5 | 9.0 |
| Treatment temperature (° C.) | 40 | 25 | 25 | 25 |
| Treatment duration (s) | 60 | 30 | 30 | 30 |
| Evaluation results | | | | |
| Appearance | ○ | ○ (gloss loss) | ○ | ○ |
| Moisture resistance | ○ | X | ○ | ○ |
| Heat resistance | ○ | X | X | X |
| Adhesiveness to resin 1 | X | ○ | ○ | ○ |
| Adhesiveness to resin 2 | X | ○ | ○ | ○ |
| Solder wettability | ○ | X | X | X |

INDUSTRIAL APPLICABILITY

The surface-treating agent of the present invention can improve the moisture resistance, heat resistance, adhesiveness to a resin and solder wettability of a metal.

The invention claimed is:

1. A surface-treating solution for a metal substrate, comprising a tetrazole derivative represented by formula 1 and/or a salt thereof in a concentration of between 0.05 g/l and 100 g/l

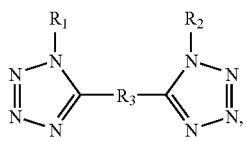

(1)

wherein $R_1$ and $R_2$ each independently represent a hydrogen atom, a halogen atom, or an alkyl group, alkenyl group, alkinyl group, aryl group, aralkyl group or benzyl group, which each have a carbon number of not more than 10, and a group having added thereto a halogen atom, a hydroxyl group, a carboxyl group, an amino group or a mercapto group, or represent an amino group, a mercapto group, a hydroxyl group or a carboxyl group; and $R_3$ represents a bond or an alkylene group, alkenylene group, alkinylene group, arylene group or aralkylene group, which each have a carbon number of not more than 10, and a group having added thereto a halogen atom, a hydroxyl group, a carboxyl group, an amino group, a mercapto group, an azo group, a sulfide group, or a disulfide group, or represents an azo group (—N═N—), a sulfide group (—S—), or a disulfide group (—S—S—), and a solvent.

2. A surface-treating solution for a metal substrate according to claim 1, further containing a metal or a metal compound.

3. A surface-treating solution for a metal substrate according to claim 1, wherein $R_1$ and $R_2$ are hydrogen atoms; and $R_3$ represents a bond, an azo group, a sulfide group, or a disulfide group.

4. A surface-treating solution for a metal substrate according to claim 1, wherein $R_1$ or $R_2$ is not a hydrogen atom.

5. A surface-treating solution for a metal substrate according to claim 1, wherein said tetrazole derivative is selected from the group consisting of 5,5'-bi-1H-tetrazole, 5,5'-bi-1-methyltetrazole, 5,5'-bi-1-phenyltetrazole, 5,5'-bi-1-mercaptotetrazole, 5,5'-bi-1-chlorotetrazole, 5,5'-ethylenebis-1-methyltetrazole, 5,5'-ethylenebis-1-phenyltetrazole, 5,5'-ethylenebis-1-mercaptotetrazole, 5,5'-ethylenebis-1-chlorotetrazole, 5,5'-azobis-1H-tetrazole, 5,5'-azobis-1-methyltetrazole, 5,5'-azobis-1-phenyltetrazole, 5,5'-azobis-1-mercaptotetrazole, 5,5'-azobis-1-chlorotetrazole, 5,5'-disulfidebis-1H-tetrazole, 5,5'-disulfidebis-1-methyltetrazole, 5,5'-disulfidebis-1-phenyltetrazole, 5,5'-disulfidebis-1-mercaptotetrazole, and 5,5'-disulfidebis-1-chlorotetrazole.

6. A surface-treating solution for a metal substrate according to claim 3, further containing a metal or a metal compound.

7. A surface-treating solution for a metal substrate according to claim 4, further containing a metal or a metal compound.

8. A surface-treating solution for a metal substrate according to claim 5, further containing a metal or a metal compound.

9. A surface-treating solution for a metal substrate according to claim 1, wherein the solvent is water.

10. A surface-treating solution for a metal substrate according to claim 2, wherein the metal and metal compounds are selected from the group consisting of zinc, manganese, chromium, tin, iron, nickel, cobalt, copper, gold, silver, platinum, palladium, rhodium, ruthenium, and compounds thereof.

11. A method of treating the surface of a metal substrate comprising the step of contacting the metal substrate's surface with the surface-treating solution of claim 1.

* * * * *